United States Patent
Koebner

[11] 3,946,037
[45] Mar. 23, 1976

[54] SULFONATION OF AROMATIC COMPOUNDS
[76] Inventor: Adolf Koebner, The Retreat, St. Bees, Cumberland, England
[22] Filed: Oct. 30, 1973
[21] Appl. No.: 411,054

[30] Foreign Application Priority Data
Oct. 30, 1972 United Kingdom............... 49928/72

[52] U.S. Cl....... 260/329 S; 260/505 C; 260/505 E; 260/512 R; 260/512 C
[51] Int. Cl.².............. C07D 333/00; C07C 143/24
[58] Field of Search......... 260/505 E, 505 C, 505 S, 260/512 R, 512 C, 329 S, 513 R

[56] References Cited
UNITED STATES PATENTS

| | | | |
|---|---|---|---|
| 2,616,936 | 11/1952 | Mammen et al. ............... | 260/513 R |
| 2,704,295 | 3/1955 | Gilbert et al. ................... | 260/505 E |
| 2,798,089 | 7/1957 | Norwood et al. ............... | 260/505 E |
| 2,832,801 | 4/1958 | Berstein ......................... | 260/505 S |
| 3,232,976 | 2/1966 | Lohr ............................... | 260/505 S |
| 3,248,413 | 4/1966 | Motl ............................... | 260/505 S |
| 3,270,038 | 8/1966 | Marshall et al. ................ | 260/505 S |
| 3,410,895 | 11/1968 | Graf et al. ....................... | 260/505 C |

OTHER PUBLICATIONS
Gilbert, "Sulfonation and Related Reactions" pp. 66–69 (1965).

Primary Examiner—James O. Thomas, Jr.
Assistant Examiner—Nicky Chan
Attorney, Agent, or Firm—Depaoli & O'Brien

[57] ABSTRACT

A process for the sulfonation of aromatic compounds wherein an aromatic substance consisting of one or more aromatic compounds is brought to boiling at a temperature not greater than 100°C under a pressure of from 0.1 mm Hg to atmospheric pressure, gaseous sulfur trioxide is introduced thereinto, thereby causing it to continue to boil, the aromatic substance thus volatilized is reconverted to liquid in a heat-exchanger and is recycled to the reaction chamber, and the pressure in the reaction chamber and the rate at which the gaseous sulfur trioxide is introduced into the aromatic substance are controlled to ensure that the amount of liquid aromatic substance present in the reaction chamber and available for participation in the sulfonation reaction is always in excess of that amount of said aromatic substance capable of reacting with the gaseous sulfur trioxide in contact with the aromatic substance in the reaction chamber and that the temperature of the reaction mixture is a temperature of 100°C or below.

3 Claims, 2 Drawing Figures 3,946,037

SULFONATION OF AROMATIC COMPOUNDS

This invention concerns improvements in or relating to the sulfonation of aromatic compounds.

BACKGROUND OF THE INVENTION

Aromatic sulfonic acids, either as such or in the form of their salts with organic or inorganic bases, are widely used. For instance, xylene sulfonates and toluene sulfonates are much used as hydrotropic agents in the detergent industry. Aromatic sulfonic acids are also important intermediates in many synthetic processes in organic chemistry, since the sulfonic acid group is relatively easily replaced by other substituent groups.

Such aromatic sulfonic acids are usually prepared by reacting the corresponding unsulfonated aromatic compound with a sulfonating agent. In the past concentrated sulfuric acid has been the principal sulfonating agent employed, but oleum (which is a solution of sulfur trioxide in concentrated sulfuric acid) and, in certain instances, sulfur trioxide itself, have also been used.

The use of sulfuric acid to effect sulfonation always results, by virtue of the reaction involved, in the production of water. This water progressively dilutes the sulfuric acid employed until sulfonation ceases, due to the concentration of the sulfuric acid becoming too low for it to effect sulfonation. The figure for the lowest concentration of sulfuric acid which will effect the sulfonation of an aromatic compound is different for different compounds, but in general the sulfonation of aromatic hydrocarbons requires a minimum concentration of sulfuric acid in the range of 78 – 90% by weight. It is apparent that, when using sulfuric acid as the sulfonating agent, it will generally be necessary to employ a large excess of sulfuric acid over that theoretically needed, in order to maintain a sufficiently high concentration of sulfuric acid for the reaction to proceed to effect a high conversion of the aromatic compound present into the corresponding sulfonic acid. When an excess of sulfuric acid is so used, the end product of the sulfonation procedure is a mixture comprising the desired aromatic sulfonic acid, any unreacted aromatic compound, by-products of the reaction and excess sulfuric acid. The separation of the main ingredients of this mixture can be achieved, but only at some cost, and with the concomitant production of substantial quantities of inorganic by-products (mainly sulfuric acid). It is clear that, if a large excess of sulfuric acid has been used in the reaction, then the amount of sulfuric acid obtained as a by-product will be substantial. This acid is difficult to dispose of, either as the acid or in the form of soluble or insoluble sulfates, particularly now when effluent requirements are becoming more stringent.

The use of oleum, instead of concentrated sulfuric acid, to some extent reduces the problem of the progressive dilution of the sulfonating agent, as the water liberated in the reaction reacts with the sulfur trioxide, which the oleum contains, to form further sulfuric acid. However, there is clearly a limit to the amount of water which can be taken up in this way by a given quantity of oleum, the precise amount depending, of course, on the percentage of sulfur trioxide contained in the oleum. Although it is possible to use less oleum than sulfuric acid, it will still normally be necessary to use an excess over that theoretically needed to react with the aromatic compound. In consequence, the problem of the subsequent separation of the desired sulfonic acid from the excess sulfuric acid at the end of the reaction and the disposal of this sulfuric acid remains.

Alternative processes which have been used for the sulfonation of aromatic compounds have involved the direct reaction of the compound with sulfur trioxide. Sulfur trioxide reacts instantaneously with aromatic compounds, and it is not necessary to use a substantial excess to effect complete sulfonation. There is, therefore, no need for the reaction product to be contaminated with substantial quantities of excess sulfonating agent. However, sulfur trioxide is very highly reactive and its reactions with aromatic compounds are extremely exothermic and difficult to control. Undesirable side reactions, particularly sulfone formation, often occur to a troublesome extent. It has, for example, been found that the addition of sulfur trioxide to benzene yields about 15 – 18% of diphenyl sulfone, and, although it is claimed that, by altering the procedure, it is possible to halve the amount of unwanted sulfone produced, the percentage obtained is still undesirably high.

In attempts to overcome these drawbacks, and to moderate and control its reactions with aromatic compounds, sulfur trioxide has been used in the presence of inert diluents. Two such procedures have been evolved. However, one of these procedures is only applicable for the sulfonation of hydrocarbons of high molecular weight, which have a very low vapour pressure at the reaction temperature, and the other procedure is expensive to implement.

The first of the two procedures involves the use of sulfur trioxide diluted with thoroughly dried air to a concentration which is generally between 1–7% v/v. This process is unsuitable for sulfonating the more volatile aromatic compounds (such as for example benzene, toluene and xylene) as the amounts of such compounds entrained in the effluent air from the process are too great, not only from the point of view of cost, but also because of the toxicity hazards and fire and explosion risks if effluent air containing substantial quantities of the aromatic compound is discharged into the atmosphere. It has not been found possible to recycle the effluent air due to its contamination with small droplets of organic matter and sulfuric acid.

Apart from the fact that the process is unsuitable for sulfonating more volatile compounds, it also has other disadvantages. Thus, the volume of air used as the diluent is large, and the drying of large volumes of air is expensive. This is particularly significant as it is not possible to recycle the air. Furthermore, the scrubbing of the effluent air prior to its release into the atmosphere is difficult, and a really satisfactory method for doing this has yet to be found.

The other process where sulfur trioxide is used in the presence of an inert diluent involves the dilution of the sulfur trioxide with an inert solvent. This process, unlike that described above, is not restricted to the sulfonation of the less volatile aromatic compounds, but is inevitably expensive since the solvent must be recovered after the reaction is completed, and some losses are inevitable. Moreover, in practice, very few solvents are satisfactory since a suitable solvent must be completely inert vis-a-vis the reactants, and preferably dissolve not only sulfur trioxide but also the aromatic compound to be sulfonated and the aromatic sulfonic acid obtained from it. Liquid sulfur dioxide has been the solvent generally used commercially hitherto. This fulfils all these requirements, but its use inevitably requires expensive pressure equipment, and refrigeration plant is necessary for its recovery. It will be apparent therefore, that the use of this process will normally only be commercially justified for the manufacture of sulfonates which sell at comparatively high prices.

One further process involving the direct reaction of sulfur trioxide with the aromatic compound has also been developed, and involves maintaining a reduced pressure or near vacuum conditions in the reaction zone, thereby increasing the inter-molecular spacing of the sulfur trioxide and hence decreasing the rate of reaction. The sulfonation by this method of alkyl benzenes having from 11 to 15 carbon atoms in the alkyl group has been described. These compounds have a comparatively low vapor pressure at the sulfonation temperature. The procedure described is, however, inapplicable to the sulfonation of aromatic compounds having a high vapour pressure at the sulfonation temperature since, when using such compounds, the quantity of vapour sucked away to the vacuum pump provided to reduce the pressure would be unacceptably high. Moreover, the process requires continuous cycling of the reaction mixture through a heat-exchanger to keep its temperature from rising to a point where side reactions would become unacceptable.

SUMMARY OF THE INVENTION

It has now been found that aromatic compounds, including those having high vapor pressures, can be sulfonated by processes in accordance with the present invention, in a manner which is readily controllable and comparatively inexpensive to operate on a commercial scale, to yield a reaction product from which it is readily possible to isolate sulfonic acid or sulfonates of relatively high purity, yet without any significant problem of disposal of excess sulfuric acid.

Accordingly this invention provides a process for the sulfonation substances having a boiling point not greater than 100°C at a pressure of 0.1 mm Hg and selected from the group consisting of aromatic compounds and mixtures thereof, said aromatic compounds being compounds susceptible to the direct action of sulfur trioxide to yield a product having a sulfonated aromatic nucleus but otherwise substantially inert under the reaction conditions to sulfur trioxide, wherein:

1. said aromatic substance at a temperature above its melting point, and thus in liquid form, is brought to boiling in a reaction chamber at a temperature selected from the group consisting of 100°C and temperatures below 100°C under a pressure of from 0.1 mm Hg to atmospheric pressure (normally about 760 mm Hg)

2. gaseous sulfur trioxide is introduced into the boiling liquid aromatic substance to react exothermically therewith, heat liberated in the exothermic sulfonation reaction causing said liquid aromatic substance to continue to boil and furnishing the latent heat of volatilization of the said liquid aromatic substance 3. the aromatic substance thus volatilized is reconverted to liquid in a heat-exchanger, so that the latent heat of volatilization is given up in the heat-exchanger and heat liberated in the sulfonation reaction is thus removed from the reaction chamber 4. the aromatic substance reconverted to liquid in the heat-exchanger is recycled to the reaction chamber, and 5. the pressure in the reaction chamber and the rate at which the gaseous sulfur trioxide is introduced into the liquid aromatic substance are so controlled that the aromatic substance is volatilized, reconverted to the liquid state and recycled to the reaction chamber at a rate such as to ensure that the amount of liquid aromatic substance present in the reaction chamber and available for participation in the sulfonation reaction is always in excess of that amount of said aromatic substance capable of reacting with the gaseous sulfur trioxide in contact with the aromatic substance in the reaction chamber and that the temperature of the reaction mixture is a temperature selected from the group consisting of 100°C and temperatures below 100°C.

The processes of the present invention are applicable to the sulfonation of any aromatic substance (which term includes both single aromatic compounds and mixtures of two or more such compounds, where said aromatic compounds are selected from the group consisting of aromatic compounds having a fully conjugated ring system and heterocyclic compounds which, although not possessing a fully conjugated ring system, nevertheless have a substantial degree of aromatic character) provided naturally that the aromatic substance boils under a pressure of 0.1 mm Hg at a temperature of not more than 100°C and provided that it is susceptible to the direct action of sulfur trioxide to yield a product having a sulfonated aromatic nucleus and is otherwise substantially inert to the action of sulfur trioxide under the conditions of the process.

It is believed to be well within the competence of any chemist to determine whether any particular compound meets these requirements. However, for general guidance it may be added that aromatic substances which boil under normal atmospheric pressure at temperatures of from 80°C to 250°C will normally boil under a pressure of 0.1 mm Hg at temperatures of not more than 100°C.

An aromatic compound to be susceptible to sulfonation by the process of this invention must include the group

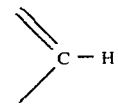

in the aromatic nucleus, and the aromatic substances most frequently sulfonated by the process of this invention will be selected from the group consisting of aromatic compounds and mixtures thereof, said aromatic compounds being represented by the formula:

wherein A represents the remainder of an aromatic ring system selected from the group consisting of aromatic hydrocarbons, thiophene and substituted derivatives of aromatic hydrocarbons and thiophene wherein all the substituent groups are substantially inert to the action of sulfur trioxide at a temperature at which sulfonation of the aromatic nucleus can be effected by sulfur trioxide.

While a very large number of aromatic compounds may be sulfonated by the processes of the present invention, the most important classes of aromatic compounds for most industrial purposes are one-ring and two-ring hydrocarbon systems (e.g. benzene and naphthalene) and thiophene, as well as substituted derivatives of all these compounds.

Hence, the sulfonation process of the present invention is particularly applicable to aromatic substances selected from the group consisting of aromatic compounds and mixtures thereof, said aromatic compounds. being represented by the formula

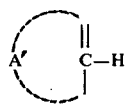

wherein A' represents the remainder of a ring system selected from the group consisting of benzene, naphthalene, thiophene, and substituted derivatives of benzene, naphthalene and thiophene wherein all the substituent groups are substantially inert to the action of sulfur trioxide at a temperature at which the sulfonation of the aromatic nucleus can be effected by sulfur trioxide.

Any aromatic substance may be sulfonated by the process of this invention provided that it conforms to the requirements that it is susceptible to the direct action of sulfur trioxide to yield a product having a sulfonated aromatic nucleus and is otherwise substantially inert to the action of sulfur trioxide under the conditions of the process, and provided also that it has a boiling point, under a pressure of 0.1 mm Hg, of 100°C or less.

The temperature at which an aromatic compound boils will depend upon the number of substituent groups which the compound contains. In general, the greater the number of substituent groups of a particular type, the higher the boiling point, but substitution by some substituent groups raises the boiling point of an aromatic compound more than substitution by other groups. It is believed to be well within the competence of any chemist to determine whether an aromatic substance is susceptible to the direct action of sulfur trioxide to yield a product having a sulfonated aromatic nucleus and is otherwise inert to the action of sulfur trioxide and boils, under a pressure of 0.1 mm Hg, at a temperature of not more than 100°C, and thus is suitable for sulfonation by the process of the invention. However, for general guidance, it may be said that the aromatic substances suitable for the process of the invention are those selected from the group consisting of aromatic compounds and mixtures thereof, said aromatic compounds being compounds containing from 1 to 10

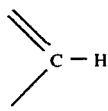

radicals where C is a carbon atom of an aromatic nucleus, selected from the group consisting of compounds containing from 6 to 14 carbon atoms and compounds containing from 6 to 14 carbon-equivalents, where
 1 carbon atom is taken as 1 carbon-equivalent
 1 fluorine atom is taken as 1 carbon-equivalent
 1 chlorine atom is taken as 2 carbon-equivalents
 1 bromine atom is taken as 3 carbon-equivalents
 1 iodine atom is taken as 6 carbon-equivalents
 1 —O— radical is taken as 1 carbon-equivalent
 1 —S— radical is taken as 2 carbon-equivalents
 1 $NO_2$ radical is taken as 6 carbon-equivalents and represented by a formula selected from the group consisting of Formulae I, II, III and IV below:

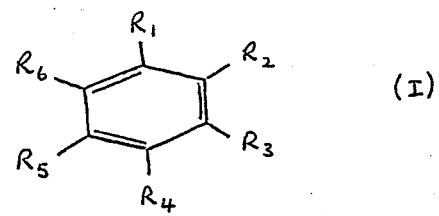

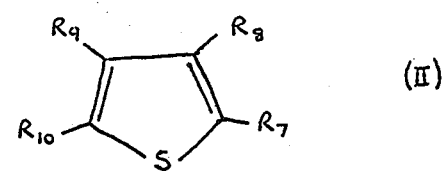

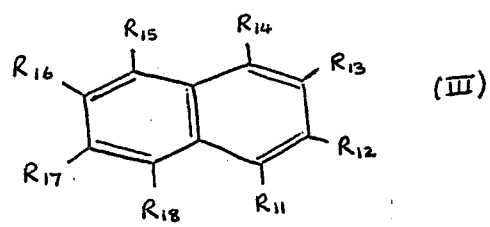

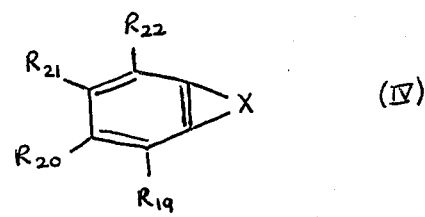

where the radicals $R_1 - R_{10}$ are selected from the group consisting of $NO_2$, F, Cl, Br, I, alkyl containing 1

– 8 carbon atoms, phenyl, benzyl, ethyl-phenyl, phenyl-ethyl, methyl-benzyl, alkoxy containing 1 – 7 carbon atoms, phenoxy, methyl-phenoxy, phenoxy-methyl and H, and where the radicals $R_{11} - R_{18}$ are selected from the group consisting of F, Cl, Br, alkyl containing 1 – 4 carbon atoms, alkoxy containing 1 – 3 carbon atoms and H, and where $R_{19} - R_{22}$ are selected from the group consisting of F, Cl, Br, alkyl containing 1 – 5 carbon atoms, alkoxy containing 1 – 4 carbon atoms and H, and where X is selected from the group consisting of saturated aliphatic hydrocarbon radicals containing 4 – 8 carbon atoms and alkoxy substituted saturated aliphatic hydrocarbon radicals containing 4 – 7 carbon atoms in all and 3 – 4 of the carbon atoms in X together with the two carbon atoms of the aromatic nucleus to which X is joined, form a ring selected from the group consisting of 5 membered rings and 6 membered rings.

Examples of compounds within Formula I above are:

benzene, toluene, ethyl-benzene, fluorobenzene, chlorobenzene, bromobenzene, iodobenzene, nitrobenzene, pentamethyl-benzene, octyl-benzene, cumene, pseudo-cumene, para-cymene, mesitylene, anisole and phenetole and all isomeric forms of xylene, ethyl-toluene, fluorotoluene, monochlorotoluene, monobromotoluene, monoiodotoluene, dichlorobenzene, trichlorobenzene, tetrachlorobenzene, tetrafluorobenzene, dibromobenzene, diethoxybenzene, nitrotoluene, monochlorotoluene, monobromotoluene, bromoxylene, dibromoxylene, dibromotoluene, iodotoluene, iodoxylene, chlorophenetole, nitroanisole and monochloronitrobenzene.

Examples of compounds within Formula II above are:

thiophene and all isomeric forms of methylthiophene, dimethylthiophene, ethyl thiophene, octyl thiophene, monochlorothiophene, monobromothiophene, monoiodothiophene, monofluorothiophene, mononitrothiophene, methoxy-thiophene and heptoxy-thiophene.

Examples of compounds within Formula III above are:

naphthalene and all isomeric forms of methylnapthalene, monofluoronapthalene, monochloronaphthalene, dimethylnaphthalene, ethyl-naphthalene, monochloromethylnaphthalene, monochloroethylnapthalene, methyl ethyl naphthalene, isopropylnaphthalene and diethylnapthalene.

Examples of compounds within Formula IV above are:

tetrahydronaphthalene and indane and all isomeric forms of methyltetrahydronaphthalene, ethyltetrahydronaphthalene, monofluorotetrahydronaphthalene and monochlorotetrahydronaphthalene (the fluorine or chlorine atom in the two last-named compounds being attached to a carbon atom in the aromatic ring), methoxytetrahydronaphthalene, ethoxytetrahydronaphthalene, dimethoxytetrahydronaphthalene, methylindane, pentyl-indane and monochloro-indane and monobromoindane (the chlorine or bromine atoms in the two last-named compounds being attached to a carbon atom in the aromatic ring).

It is not necessary for the aromatic compound which is to be sulfonated by the process of the present invention to be pure. Not only can mixtures of different aromatic compounds be employed as the aromatic substance, in the manner already indicated, but it is also frequently convenient to use commercially available aromatic materials which are mixtures of different isomers. It will also frequently be convenient to use commercially available aromatic substances which contain impurities, although it is obvious that it is generally undesirable for the aromatic substance to contain substantial quantities of unsulfonatable impurities which are likely to impair the usefulness of the end product of the sulfonation procedure, or to contain impurities which will react with the sulfur trioxide to produce tar or other undesirable products.

The sulfonation processes of the present invention must be carried out at a temperature at or below 100°C, since side reactions and darkening of the product take place to a significant extent above this temperature. It is preferred in practice to carry out sulfonation by the process at a temperature of 20°C or above, in order that the heat-exchanger employed may be a water-cooled condenser; and at 80°C or below in order that undesirable side reactions are minimized. Preferred temperatures are from 40°C to 60°C.

Since most aromatic compounds boil under normal atmospheric pressure at a temperature of above 100°C, it is normally necessary, when employing such compounds, to effect the process of the present invention under reduced pressure. Even using benzene which under normal atmospheric pressure boils at a temperature of about 80°C and can therefore be sulfonated in accordance with the present invention at atmospheric pressure, it is often preferred to effect the process under reduced pressure so as to be able to work at a lower temperature. It is in practice often convenient to work at a pressure ranging from 3 to 700 mm of mercury; though the process can in fact be effected at a pressure even as low as 0.1 mm Hg, and will most often be effected at a pressure of from 25 mm Hg to 400 mm Hg.

The sulfur trioxide employed in the process of the invention may be provided in any convenient way. While the use of sulfur trioxide diluted with air or another inert gas is not excluded, this could give rise to entrainment losses which will become more and more unacceptable as the degree of dilution increases. Hence no advantage is usually seen in diluting the sulfur trioxide, which therefore should normally be used undiluted, thus in the state of purity in which it is commercially available. Thus the sources of sulfur trioxide may conveniently be either commercially available stabilized sulfur trioxide or oleum. The sulfur trioxide thus generated may conveniently be merely aspirated into the aromatic substance.

In the processes of the prior art, it has been normal, when sulfonating with sulfuric acid or oleum, to use an excess of sulfonating agent over that theoretically needed, in order to convert as nearly as possible the whole of the aromatic compound present to the corresponding sulfonic acid. Even when sulfur trioxide has been used as the sulfonating agent, it has been usual to employ sufficient sulfur trioxide to convert all or nearly all of the aromatic substance to the corresponding sulfonic acid. In the processes of the present invention, however, although sulfur trioxide is used as the sulfonating agent, it is the aromatic substance which is employed in excess. Inevitably this means that the reaction product contains some amount of unreacted aromatic compound. However, this generally is easily removable by distillation to yield anhydrous sulfonic acids of well over 95% purity.

In the processes of the present invention the sulfur trioxide is passed into the aromatic substance in the liquid state at its boiling point. The highly exothermic reaction which occurs causes the aromatic substance to boil thereby controlling the temperature of the aromatic substance and also causing thorough mixing. This considerably reduces the risk of local overheating and hence charring. The aromatic substance volatilized in the process is reconverted to liquid by cooling in the heat-exchanger and is returned to the reaction mixture. Although any suitable heat-exchanger may be employed, the heat-exchanger is most conveniently a water-cooled condenser. The flow of the sulfur trioxide should be controlled so that the substance is not volatilized by the heat of the reaction more rapidly than the heat-exchanger is able to reconvert it to the liquid state.

It has been found that the absorption of sulfur trioxide in the process of the present invention is almost quantitative in the liquid phase, but the condensed liquid aromatic compound being returned to the reaction mixture can provide further scrubbing of any trace of sulfur trioxide which may have escaped reaction.

The excess of the aromatic substance employed when operating the process as a batch process preferably amounts to from 1 to 100% by weight above that theoretically needed to react with the sulfur trioxide used in the process. It is however unnecessary to use accurately weighed or measured proportions of the reactants, so long as an excess of the aromatic substance is present in the reaction chamber all the time during the reaction. The fact that it is not necessary accurately to control the proportions of the reactants is especially convenient when the reaction is conducted as a continuous process, since it eases the technical problems of measuring and controlling the sulfur trioxide stream. The use of an excess of unreacted aromatic substance assists in maintaining the boiling of the reaction mixture at a steady temperature, and in controlling the viscosity of the reaction mixture. The use of an excess of the aromatic substance also minimises undesirable sulfone formation. Even by this process however some sulfone may be produced, and in order to reduce the amount a sulfone depressor (for example, acetic acid or acetic anhydride) may be incorporated into the reaction medium.

The process of the present invention yields a mixture comprising mainly the desired aromatic sulfonic acid, together with unreacted aromatic compound and certain impurities. The sulfonic acid may generally be isolated quite readily by conventional methods. Simple distillation of the excess aromatic compound (preferably in vacuo) often yields the anhydrous sulfonic acid in a state of purity well over 95%, the major contaminant being the corresponding sulfone formed as a by-product during the reaction. Alternatively, instead of removing unreacted aromatic substance by distillation, it is possible to add water or an aqueous solution of an alkali with cooling to the reaction product, and the resultant mixture will on standing separate into two phases. Provided that the relative density of the aromatic substance is less than the relative density of the solution of sulfonic acid or sulfonate formed, the lower layer contains the sulfonic acid or sulfonate formed, and the unreacted aromatic compound remains as the top layer and may be removed by decantation. The lower layer may then be boiled, preferably under reduced pressure, to remove any remaining unreacted aromatic substance, and leave an aqueous solution of the desired sulfonic acid or sulfonate salt. This latter method removes from the sulfonic acid or sulfonate solution most of the sulfones, whose formation always to some extent accompanies the production of sulfonic acids by sulfonation with sulfur trioxide.

Naturally, any aromatic compound recovered may be recycled in the process of the invention, if necessary after drying and/or purification by distillation.

Where it is possible to do so, the process can advantageously be operated continuously, by feeding the aromatic substance continuously into the reaction chamber and bringing it to boiling, introducing the sulfur trioxide continuously into the boiling aromatic substance therein, withdrawing reaction mixture continuously from the reaction chamber, and separating from the reaction mixture the unreacted aromatic substance, purifying and recycling it to the reaction chamber.

The invention also extends to any aromatic sulfonic acid and the salts thereof whenever the sulfonic acid is prepared by the sulfonation process of this invention.

DETAILED DESCRIPTION OF THE INVENTION

The invention will now be described, though only by way of illustration, with reference to the apparatus shown in the accompanying drawings. Details of preferred reagents, conditions and techniques employed in the processes of the present invention are given in the Examples which follow the description with reference to the drawings.

GENERAL BATCH PRODUCTION

Figure 1:
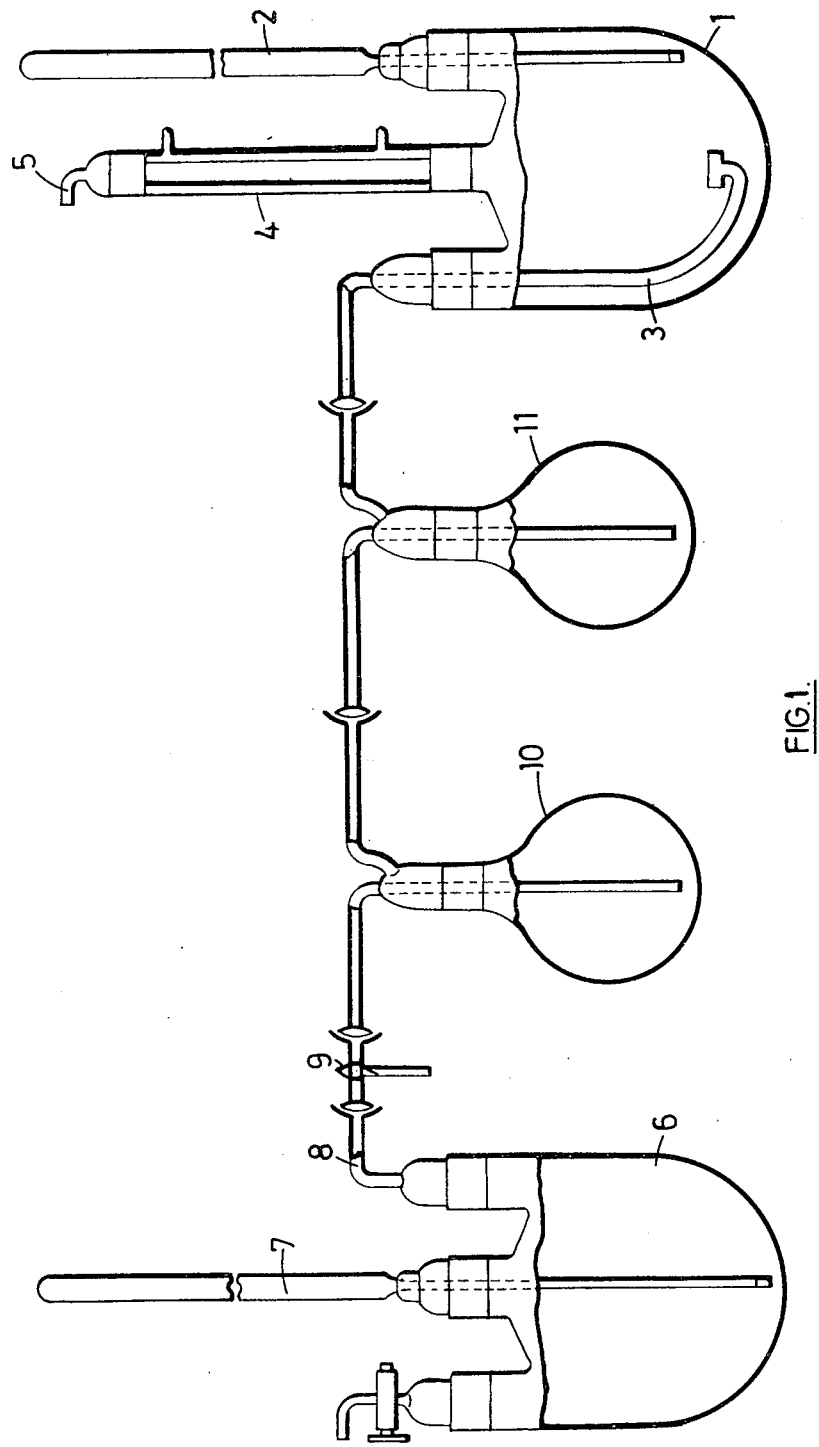

An apparatus for carrying out a reaction batchwise in accordance with the present invention is illustrated in FIG. 1 of the accompanying drawings. In this apparatus, a three-necked flask 1 is employed as the reaction vessel, and is fitted with a thermometer 2, a gas inlet tube 3 reaching to the bottom of the flask and a reflux condenser 4 which is connected to a vacuum pump by the line 5. A two-necked flask 6, fitted with a thermometer 7 and a vapour outlet line 8, is provided as sulfur trioxide generator. The two flasks are connected through a tap unit 9 and two empty flasks 10 and 11 which serve as safety traps. The appropriate amount of the dry aromatic substance to be sulfonated is placed in the reaction vessel 1, and a suitable amount of sulfur trioxide (usually for preference in a molecular ratio of aromatic substance to sulfur trioxide of approximately 2:1) in stabilized liquid form is placed in the flask 6. The aromatic substance is then heated to the desired reaction temperature and, on reduction of the pressure, begins to reflux. The sulfur trioxide generator heated to a predetermined temperature is then connected via the tap 9 to the reactor 1 through the vapor line of the generator and gas inlet line of the latter. Sulfur trioxide evaporates into the partially-evacuated system and passes into the boiling aromatic substance which remains vigorously agitated by ebullition throughout the reaction. Gentle warming of the trioxide generator is maintained throughout the reaction to aid evaporation. The reaction vessel itself need not be heated at all since the strongly exothermic reaction maintains the mixure at the boil whilst any excess heat of reaction is removed as latent heat of volatilization of the aromatic substance.

The reaction is completed when all the sulfur trioxide has evaporated and passed from the generator into the reaction vessel. At the same time reflux in the reaction vessel ceases as no further heat is evolved.

GENERAL CONTINUOUS PRODUCTION

Figure 2:
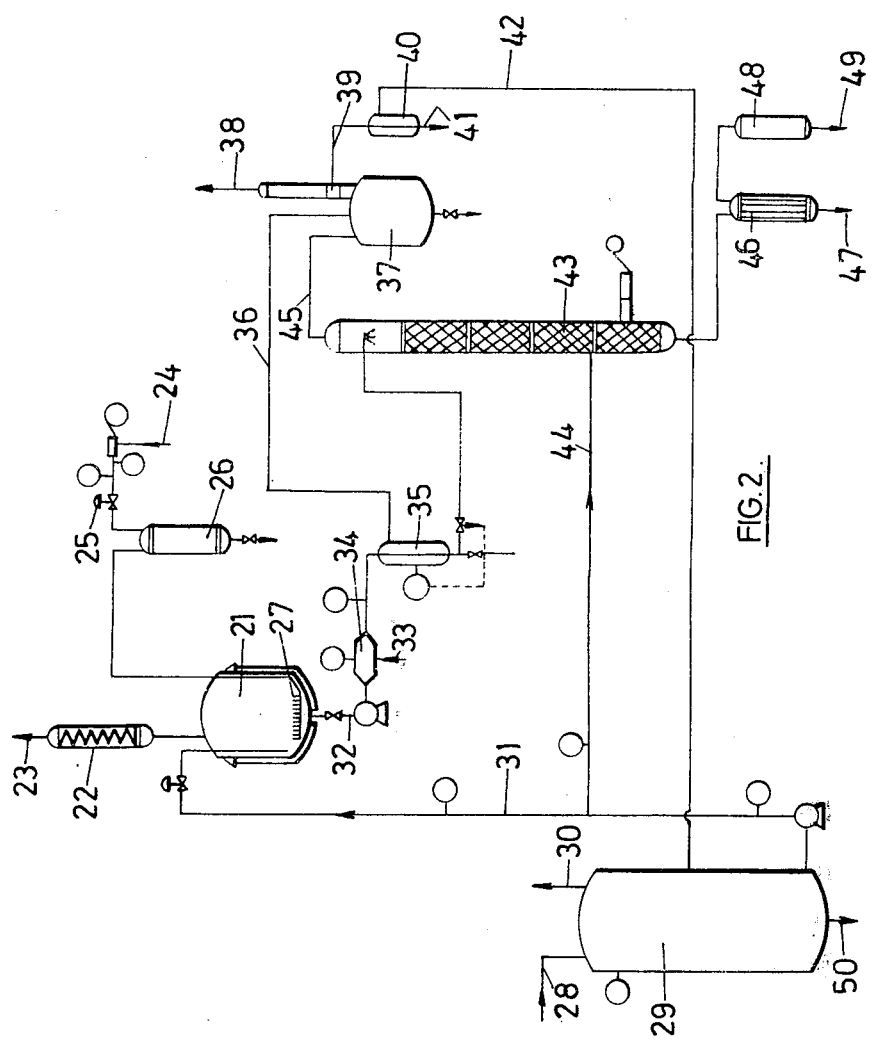

A plant for carrying out a process of the present invention for the sulfonation in a continuous manner of an aromatic substance having a relative density of less than 1 is illustrated in FIG. 2 of the accompanying drawings.

In this plant a reactor 21 is provided with a reflux condenser 22 itself attached to a vacuum line 23. Sulfur trioxide is supplied via a line 24 regulated by a tap 25 to an evaporator 26 and thence to a gas inlet nozzle 27 at the base of the reactor 21. The aromatic substance to be sulfonated is supplied from bulk storage via a line 28 to a feed tank 29 having a safety vent 30. From this tank the aromatic substance is fed to the reactor 21 by the line 31. Reaction mixture may be continuously withdrawn from the base of the reactor by the line 32 and mixed with water or aqueous alkali fed by the line 33 in an in-line mixer unit 34 from where it passes to a separator 35 with a recycle circuit. The unreacted aromatic substance is taken from the separator 35 as the upper layer and fed via line 36 to a distillation vessel 37 attached to a vacuum line 38. After vacuum distillation the unreacted aromatic substance is passed via a line 39 into a further separator 40 from where water is removed by the line 41 and the unreacted aromatic substance is then returned via the line 42 to the feed tank 29.

The aqueous sulfonic acid or sulfonate solution is fed from the separator 35 to the top of an extraction column 43, into the middle of which is passed some of the aromatic substance taken by a line 44 from the supply line 31. The aromatic substance removed overhead from the extraction column is passed by line 45 to the distillation vessel 37. The aqueous sulfonic acid or sulfonate is led from the base of the extraction column 43 to a stripper 46 from which the final traces of unreacted aromatic substance are removed and the pure final product is then removed from the plant by a line 47. The small quantities of water and unreacted aromatic substance removed in this final stripper 46 are condensed in vessel 48 and then recycled via line 49. Some water is also contained in the recycle line 42 and this accumulates at the bottom of the feed tank 29 from which it may be removed by the drain plug 50.

EXAMPLE 1 — PREPARATION OF BENZENE SULFONIC ACID

Mono-sulfonation of benzene was carried out in the apparatus of FIG. 1. Dry benzene (390 g., 5 gram molecules) was placed in the three-necked reaction flask (1 litre capacity) together with acetic anhydride (1 g) which was added to suppress sulfone formation. The reaction flask was heated to 40°C and the pressure gradually reduced until the benzene refluxed vigorously at 400 mm Hg. The sulfur trioxide generator was charged with liquid, stabilized sulfur trioxide (200 g, 2.5 gram molecules) and the two flasks were connected to allow the sulfur trioxide to be aspirated into the reaction flask. External heating of the reaction flask was discontinued but the trioxide generator was gently warmed to maintain an internal temperature of 30°C to aid evaporation. The reaction was completed when all the sulfur trioxide had been evaporated from the generator and had passed into the reaction vessel. At this point reflux ceased. Anhydrous benzene sulfonic acid was isolated by distilling off the excess benzene in vacuo, leaving a light amber coloured oil which crystallized slowly when kept in a desiccator over concentrated sulfuric acid. The sulfonic acid was contaminated by 0.2% sulfuric acid and 1.5% diphenyl sulfone. The yield was 98% calculated with respect to the amount of sulfur trioxide employed.

The above-described procedure, when applied to thiophene (using the reactants in the same molecular proportions as above) and with appropriate adjustment of pressure to secure boiling at about 40°C, yields a similar high degree of conversion to thiophene sulfonic acid, usually in the form of a mixture of the isomers thereof.

EXAMPLE 2 — PREPARATION OF P-CHLOROBENZENE SULFONIC ACID

In the apparatus described in FIG. 1 chlorobenzene was sulfonated at 60°C and under a pressure of 75 mm Hg. The reaction vessel 1 was charged with chlorobenzene (225 g., 2 gram molecules) and acetic acid (1 g) was added to suppress sulfone formation. Oleum (200 g 65% sulfur trioxide content) was placed into the trioxide generator which was accurately weighed. During the reaction the sulfur trioxide generator was gradually warmed to about 50°C and the reaction was stopped when the generator had lost 80 g in weight. Water (190 g) was then carefully added to the reaction mixture which separated into two layers. The lower aqueous sulfonic acid phase was drawn off and boiled until free from chlorobenzene. The yield of p-chlorobenzene sulfonic acid in the form of a 50% aqueous solution was almost quantitative.

The above-described procedure, when applied (using the reactants in the same molecular proportions as above) to the following compounds

| | |
|---|---|
| toluene | (methyl-benzene) |
| cumene | (isopropyl-benzene) |
| anisole | (methoxy-benzene) |
| meta-chloro-toluene | |
| 2-ethyl-chloro-benzene | | and with appropriate adjustment of pressure to secure boiling at about 60°C, yields a high degree of conversion to the corresponding sulfonic acid, usually in the form of a mixture of the isomers thereof.

EXAMPLE 3 — SULFONATION OF SOLVENT NAPHTHA

Solvent naphtha (an aromatic fraction obtained from coal tar or petroleum sources, boiling under atmospheric pressure in the range 160° – 190°C, and containing a large number of isomeric and homologous hydrocarbons such as pseudocumene, hemimellitene, mesitylene, p-cymene and ethyl-toluene) was sulfonated by the method of Example 1, but at 75°C and under a pressure of 30 mm Hg. The solvent naphtha (240 g, 2 gram molecules) containing acetic acid (1 g), was reacted with sulfur trioxide (80 g, 1 gram molecule). The product was a complex mixture of isomers of sulfonic acids derived from the mixed aromatic hydrocarbon feed and was isolated as an almost colourless 30% aqueous solution by the method described in Example 2.

The above-described procedure, when applied (using the reactants in the same molecular proportions as above) to the following compounds

| | |
|---|---|
| xylene | (o, m and p dimethyl-benzene) |
| para-cymene | (p-isopropyl-toluene) |
| phenetole | (ethoxy-benzene) |
| meta-bromo-toluene | | and with appropriate adjustment of pressure to secure boiling at about 75°C, yields a high degree of conversion to the corresponding sulfonic acid, usually in the form of a mixture of the isomers thereof.

I claim:

1. A process for the sulfonation of aromatic substances and mixtures thereof selected from the group consisting of benzene, toluene, ethyl-benzene, fluorobenzene, chlorobenzene, bromobenzene, iodobenzene, nitrobenzene, pentamethyl-benzene, octyl-benzene, cumene, pseudo-cumene, para-cymene, mesitylene, anisole, phenetole, thiophene, naphthalene, tetrahydronaphthalene and indane, and all isomeric forms of xylene, ethyl-toluene, fluorotoluene, monochlorotoluene, monobromotoluene, monoiodotoluene, dichlorobenzene, trichlorobenzene, tetrachlorobenzene, tetrafluorobenzene, dibromobenzene, diethoxybenzene, nitrotoluene, monochlorotoluene, monobromotoluene, bromoxylene, dibromoxylene, dibromotoluene, iodotoluene, iodoxylene, chlorophenetole, nitroanisole, monochloronitrobenzene, methylthiophene, dimethylthiophene, ethylthiophene, octyl thiophene, monochlorothiophene, monobromothiophene, monoiodothiophene, monofluorothiophene, monoitrothiophene, methoxy-thiophene, heptoxy-thiophene, methylnaphthalene, monofluoronaphthalene, monochloronaphthalene, dimethylnaphthalene, ethyl naphthalene, monochloromethylnaphthalene, monochloroethylnaphthalene, methyl ethyl naphthalene, isopropyl-naphthalene, diethylnaphthalene, methyltetrahydronaphthalene, ethyltetrahydronaphthalene, monofluorotetrahydronaphthalene, monochlorotetrahydronaphthalene, (the fluorine or chlorine atom in the two compounds last named being attached to a carbon atom in the aromatic ring), methoxytetrahydronaphthalene, ethoxytetrahydronaphthalene, dimethoxytetrahydronaphthalene, methyl-indane, pentyl-indane and monochloro-indane and monobromo-indane where the chlorine or bromine atom in the two last-named compounds is attached to a carbon atom in the aromatic ring, in which process:
  1. said aromatic substance is brought to boiling in a reaction chamber at a temperature in the range from above the melting point of said aromatic compound to 100°C, under a pressure of from 0.1 mm Hg to atmospheric pressure,
  2. gaseous sulfur trioxide is introduced into the boiling liquid aromatic substance to react exothermically therewith, heat liberated in the exothermic sulfonation reaction causing said liquid aromatic substance to continue to boil and furnishing the latent heat of volatilization of the said liquid aromatic substance,
  3. the aromatic substance thus volatilized is reconverted to liquid in a heat-exchanger, so that the latent heat of volatilization is given up in the heat-exchanger and heat liberated in the sulfonation reaction is thus removed from the reaction chamber,
  4. the aromatic substance reconverted to liquid in the heat-exchanger is recycled to the reaction chamber,
  5. the pressure in the reaction chamber and the rate at which the gaseous sulfur trioxide is introduced into the liquid aromatic substance are so controlled that the aromatic substance is volatilized, reconverted to the liquid state and recycled to the reaction chamber at a rate such as to ensure that the amount of liquid aromatic substance present in the reaction chamber and available for participation in the sulfonation reaction is always in excess of that amount of said aromatic substance capable of reacting with the gaseous sulfur trioxide in contact with the aromatic substance in the reaction chamber and that the temperature of the reaction mixture is a temperature in the range from above the melting point of said aromatic substance to 100°C.

2. A process according to claim 1, where the process is operated continuously, the aromatic substance being continuously fed into the reaction chamber and brought to boiling, the sulfur trioxide being continuously introduced into the boiling aromatic substance therein, the reaction mixture being continuously withdrawn from the reaction chamber, and the unreacted aromatic substance being separated from the reaction mixture, purified and recycled to the reaction chamber.

3. A process for the sulfonation of an aromatic substance which is a commercially available solvent naphtha aromatic fraction obtained from coal tar and petroleum having a boiling range of from 160°C to 190°C, in which process
  1. said aromatic substance is brought to boiling in a reaction chamber at a temperature in the range from above the melting point of said aromatic compound to 100°C, under a pressure of from 0.1 mm Hg to atmospheric pressure,
  2. gaseous sulfur trioxide is introduced into the boiling liquid aromatic substance to react exothermically therewith, heat liberated in the exothermic sulfonation reaction causing said liquid aromatic substance to continue to boil and furnishing the latent heat of volatilization of the said liquid aromatic substance,
  3. the aromatic substance thus volatilized is reconverted to liquid in a heat-exchanger, so that the latent heat of volatilization is given up in the heat-exchanger and heat liberated in the sulfonation reaction is thus removed from the reaction chamber,
  4. the aromatic substance reconverted to liquid in the heat-exchanger is recycled to the reaction chamber,
  5. the pressure in the reaction chamber and the rate at which the gaseous sulfur trioxide is introduced into the liquid aromatic substance are so controlled that the aromatic substnace is volatilized, reconverted to the liquid state and recycled to the reaction chamber at a rate such as to ensure that the amount of liquid aromatic substance present in the reaction chamber and available for participation in the sulfonation reaction is always in excess of that amount of said aromatic substance capable of reacting with the gaseous sulfur trioxide in contact with the aromatic substance in the reaction chamber and that the temperature of the reaction mixture is a temperature in the range from above the melting point of said aromatic substance to 100°C.

* * * * *

UNITED STATES PATENT OFFICE
CERTIFICATE OF CORRECTION

Patent No. 3946037          Dated March 23, 1976

Inventor(s) Adolf Koebner

It is certified that error appears in the above-identified patent and that said Letters Patent are hereby corrected as shown below:

Column 1, line 27, - "he concentration" should be --the concentration--.

Column 3, line 40 - "sulfonation substances" should be --sulfonation of aromatic substances--.

*Signed and Sealed this*

*twenty-ninth* Day of June 1976

[SEAL]

Attest:

RUTH C. MASON
*Attesting Officer*

C. MARSHALL DANN
*Commissioner of Patents and Trademarks*